(12) United States Patent
Respini

(10) Patent No.: US 9,282,260 B2
(45) Date of Patent: Mar. 8, 2016

(54) VISUALIZING POLYNUCLEAR AROMATIC HYDROCARBONS WITHIN THE NEAR INFRARED SPECTRUM

(71) Applicant: Baker Hughes Incorporated, Houston, TX (US)

(72) Inventor: Marco Respini, Casaimorano (IT)

(73) Assignee: Baker Hughes Incorporated, Houston, TX (US)

( * ) Notice: Subject to any disclaimer, the term of this patent is extended or adjusted under 35 U.S.C. 154(b) by 317 days.

(21) Appl. No.: 13/849,865

(22) Filed: Mar. 25, 2013

(65) Prior Publication Data

US 2013/0265405 A1    Oct. 10, 2013

Related U.S. Application Data

(60) Provisional application No. 61/620,670, filed on Apr. 5, 2010.

(51) Int. Cl.
 *H04N 5/33* (2006.01)
 *G01N 21/359* (2014.01)
 *G01N 21/64* (2006.01)
 *G01N 21/82* (2006.01)
 *G02B 21/00* (2006.01)

(52) U.S. Cl.
 CPC .............. *H04N 5/33* (2013.01); *G01N 21/359* (2013.01); *G01N 21/6458* (2013.01); *G01N 21/82* (2013.01); *G02B 21/0004* (2013.01)

(58) Field of Classification Search
 CPC .. H04N 5/33; G02B 21/0004; G02B 21/0016; G02B 21/0032; G02B 21/06; G02B 21/3364; G02B 21/361; G01J 3/42; G01J 3/427; G01N 21/31
 USPC .......................................................... 348/79
 See application file for complete search history.

(56) References Cited

U.S. PATENT DOCUMENTS

| | | | | |
|---|---|---|---|---|
| 3,642,608 A | * | 2/1972 | Roach | C09C 1/50 208/418 |
| 3,977,962 A | * | 8/1976 | Arey, Jr. | B01J 23/74 208/112 |
| 4,283,128 A | * | 8/1981 | Meyer | G01N 15/0227 250/301 |
| 4,356,077 A | * | 10/1982 | Che | C10G 1/002 201/25 |
| 5,656,810 A | * | 8/1997 | Alfano | G01N 21/64 250/255 |
| 5,880,830 A | | 3/1999 | Schechter | |
| 5,928,954 A | | 7/1999 | Rutledge et al. | |
| 5,966,204 A | * | 10/1999 | Abe | G02B 21/086 356/51 |
| 2002/0021490 A1 | * | 2/2002 | Kasahara | G02B 21/0004 359/380 |
| 2002/0139929 A1 | * | 10/2002 | Mullins | E21B 47/102 250/255 |
| 2003/0117619 A1 | | 6/2003 | Vo-Dinh et al. | |
| 2003/0141459 A1 | * | 7/2003 | Hegazi | G01N 21/6408 250/461.1 |
| 2005/0134845 A1 | * | 6/2005 | Bordelon | G01N 15/0227 356/336 |
| 2008/0173805 A1 | * | 7/2008 | Indo | E21B 47/102 250/269.1 |
| 2011/0203353 A1 | | 8/2011 | Hough et al. | |
| 2012/0318982 A1 | * | 12/2012 | Janik | G01N 21/274 250/339.11 |

FOREIGN PATENT DOCUMENTS

| | | |
|---|---|---|
| JP | 2006528727 A | 12/2006 |
| WO | 2010151361 A1 | 12/2010 |

* cited by examiner

*Primary Examiner* — Richard Torrente
*Assistant Examiner* — Marnie Matt
(74) *Attorney, Agent, or Firm* — Mossman, Kumar & Tyler, P.C.

(57) ABSTRACT

Microscopy techniques may be used to visualize polynuclear aromatic hydrocarbons where an optical microscope is combined with an imaging device. The combination of these devices allows for images to be produced when visualized in the near infrared spectrum, such as a wavelength ranging from about 700 nm to about 2500 nm to be passed through the optical microscope.

17 Claims, 2 Drawing Sheets

VISUALIZING POLYNUCLEAR AROMATIC HYDROCARBONS WITHIN THE NEAR INFRARED SPECTRUM

CROSS-REFERENCE TO RELATED APPLICATION

This application claims the benefit of Provisional Patent Application No. 61/620,670 filed Apr. 5, 2012, which is incorporated by reference herein in its entirety.

TECHNICAL FIELD

The present invention relates to microscopy techniques for visualizing polynuclear aromatic hydrocarbons, or more particularly relates to methods of using a microscope in conjunction with an imaging device for visualizing polynuclear aromatic hydrocarbons when visualized in the near infrared spectrum.

BACKGROUND

It is often beneficial to detect polynuclear aromatic hydrocarbons (PAHs) present within oilfield fluids, and fluids derived from processing oilfield fluids during oil refining and petrochemical processes. Polynuclear aromatic hydrocarbons (PAHs), also known as polycyclic aromatic hydrocarbons or poly-aromatic hydrocarbons, occur in oil, coal, and tar deposits, and are typically found within oilfield fluids and as a result of refinery and/or petrochemical processing of such oilfield fluids. PAHs are hydrocarbon structures with fused aromatic rings and do not typically contain heteroatoms or carry substituents. Although PAHs are aromatic compounds, the degree of aromaticity may be different for each ring segment. A PAH is typically characterized by the resonance structure with the most disjoint aromatic n-sextets—i.e. benzene-like moieties.

Drilling fluids are used in operations to drill boreholes into the earth; 'drilling fluid' is typically synonymous with 'drilling mud'. One classification of drilling fluid is based on the composition of the fluid or mud. For example, drilling fluids include, but are not necessarily limited to, water-based fluids, brine-based fluids, oil-based fluids and synthetic-based fluids, which are synthetically produced rather than refined from naturally-occurring materials.

Production fluid is the fluid that flows from a formation to the surface of an oil well. These fluids may include oil, gas, water, as well as any contaminants (e.g. $H_2S$, asphaltenes, etc.) therein. The consistency and composition of the production fluid may vary. Refinery and petrochemical fluids are results of processing production fluids. These processing methods may include distillation, delayed coking, hydrocracking, visbreaking, steam cracking of gas and distillate range products.

Hydrocracking is a catalytic cracking process using an elevated partial pressure of hydrogen gas to purify the hydrocarbon stream, e.g. polynuclear aromatic hydrocarbons, from sulfur and nitrogen hetero-atom that may have byproducts, such as napthenes and alkanes. Thermal cracking is a similar process where hydrocarbons, such as crude oil, are subjected to high heat and temperature to break the molecular bonds and reduce the molecular weight of the substance being cracked. The usable components are extracted, known as fractions, and released during the cracking process. These are two types of cracking methods used in the petroleum industry to process crude oil and/or other petroleum products for commercial use.

PAHs have very unique absorbance bands for each ring structure with respect to varying wavelengths of light. For a set of isomers, each isomer may have a different absorbance spectrum, which is useful in the identification of PAHs. PAHs may also be fluorescent when the molecules absorb light, i.e. emitting characteristic wavelengths of light when they are excited. Current examples of detecting PAHs within their respective materials may include gas chromatography-mass spectrometry, liquid chromatography with ultraviolet-visible, fluorescence spectroscopic methods, and using rapid test PAH indicator strips.

Several types of PAHs may be found within asphaltenes, coke, coke precursors, oil resins, carboids, and combinations thereof. Naphthalene is the simplest of the PAHs and has two coplanar six-membered rings that share an edge. Some do not consider naphthalene to be a true PAH, but it shall be defined as a PAH for purposes related to this application. Perylene has the chemical formula $C_{20}H_{12}$ with a structure of two naphthalene molecules connected by a carbon-carbon bond at the 1 and 8 positions on both molecules. All of the carbon atoms in perylene are $sp^2$ hybridized. Coronene (also known as superbenzene) has six peri-fused benzene rings with a chemical formula of $C_{24}H_{12}$. Chrysene has four fused benzene rings and has the molecular formula $C_{18}H_{12}$. Chrysene may be a natural constituent or derived from coal tar, creosote, coal, crude oil, and plant material. Anthracene comprises three fused benzene rings with a chemical formula of $C_{14}H_{10}$.

Asphaltenes are most commonly defined as that portion of crude oil, which is insoluble in heptane. Asphaltenes exist in the form of colloidal dispersions stabilized by other components in the crude oil. They are the most polar fraction of crude oil, and often will precipitate upon pressure, temperature, and compositional changes in the oil resulting from blending or other mechanical or physicochemical processing. Asphaltene precipitation occurs in pipelines, separators, and other equipment. Once deposited, asphaltenes present numerous problems for crude oil producers. For example, asphaltene deposits can plug downhole tubulars, well-bores, choke off pipes and interfere with the functioning of separator equipment. The asphaltene deposits may also precipitate within a fluid and foul refining and/or petrochemical processes of such fluids. In addition to carbon and hydrogen in the composition, asphaltenes also may contain nitrogen, oxygen and sulfur species. Typical asphaltenes are known to have some solubilities in the oilfield fluid itself or in certain solvents like carbon disulfide, but are insoluble in solvents like light naphthas.

Coke is typically defined as a toluene, and/or an insoluble organic portion of crude oil, distillation residua, or residua from thermal/catalytic conversion processes, such as including but not limited to visbreaker tar or LC finer/H oil residuum. Coke may have PAHs dispersed therein with a ring structure of about 4 to about 5 or more condensed aromatic rings. Coke may be polymerized to a molecular weight where it is no longer soluble in crude oil or residua.

Coke precursors are the fragments that make up the coke, which may also include PAHs. Coke precursors may form from thermal cracking, dealkylation and/or dehydrogenation processes commonly used for the breaking down of complex organic molecules. They are barely soluble in the crude oil and/or residual, but they tend to precipitate. Once they precipitate, the coke precursors tend to polymerize or conglomerate into coke.

Coke and/or coke precursors are typically formed during thermal cracking and/or distillation during in situ combustion, which is a method of generating fire inside a reservoir by injecting an oxygen gas, such as air. A special heater in the well ignites the oil in the reservoir and starts a fire. The heat generated from burning the heavy hydrocarbons in situ produces hydrocarbon cracking vaporization of light hydrocarbons and reservoir water in addition to the deposition of heavier hydrocarbons known as coke.

When the oilfield fluid from a subsurface formation comes into contact with a pipe, a valve, or other production equipment of a wellbore, or when there is a decrease in temperature, pressure, or change of other conditions, these PAHs may precipitate or separate out of the oilfield fluid. While any separation or precipitation is undesirable in and by itself, it is much worse when the precipitants accumulate and stick to the equipment in the wellbore. Any precipitants sticking to the wellbore surfaces may narrow pipes; and clog wellbore perforations, various flow valves, and other wellsite and downhole locations and may result in wellsite equipment failures. It may also slow down, reduce or even totally prevent the flow of oilfield fluids into the wellbore and/or out of the wellhead.

Similarly, undetected precipitations and accumulations of PAHs in a pipeline for transferring crude oil could result in loss of oil flow and/or equipment failure. Crude oil storage facilities could have maintenance or capacity problems if PAH precipitations remain undetected for an extended period of time. Precipitation and accumulation of PAHs may also occur during refining of production fluids within the heater when trying to separate the production fluids into fractions of different boiling points. Finally, the precipitation of PAHs may also occur during the refinery and petrochemical processing of lighter distillate refinery streams such as, but not limited to, gas, gasoline, gasoils, and the like by thermal and/or catalytic conversion units. These include Fluid Catalytic Cracking (FCC unit) and steam cracking/ethylene cracking units in petrochemical plants.

Thus, it would be desirable if methods could be devised to better detect the presence, amounts and/or properties of polynuclear aromatic compounds commonly found within the aforementioned fluids.

SUMMARY

There is provided, in one form, a method for using an optical microscope to produce an image of polynuclear aromatic hydrocarbons by passing a wavelength therethrough ranging from about 700 nm to about 2500 nm. An imaging device may be combined with the optical microscope to capture the image produced by the optical microscope.

There is further provided in another non-limiting embodiment where a sample has been collected from an oilfield fluid having the polynuclear aromatic hydrocarbons. The oilfield fluid may be, but is not limited to a drilling fluid, a completion fluid, a production fluid, a servicing fluid, crude oil, a refinery fluid, and combinations thereof. The polynuclear aromatic hydrocarbons may be, but are not limited to asphaltenes, coke, coke precursors, naphthalene, perylene, coronene, chrysene, anthracene, and combinations thereof.

In another non-limiting embodiment, the imaging device may be configured to filter a wavelength ranging from about 700 nm to about 2500 nm.

Microscopy techniques may be used to visualize polynuclear aromatic hydrocarbons where a microscope may be paired with an imaging device to produce images in the near infrared spectrum.

DETAILED DESCRIPTION

Figure 1:
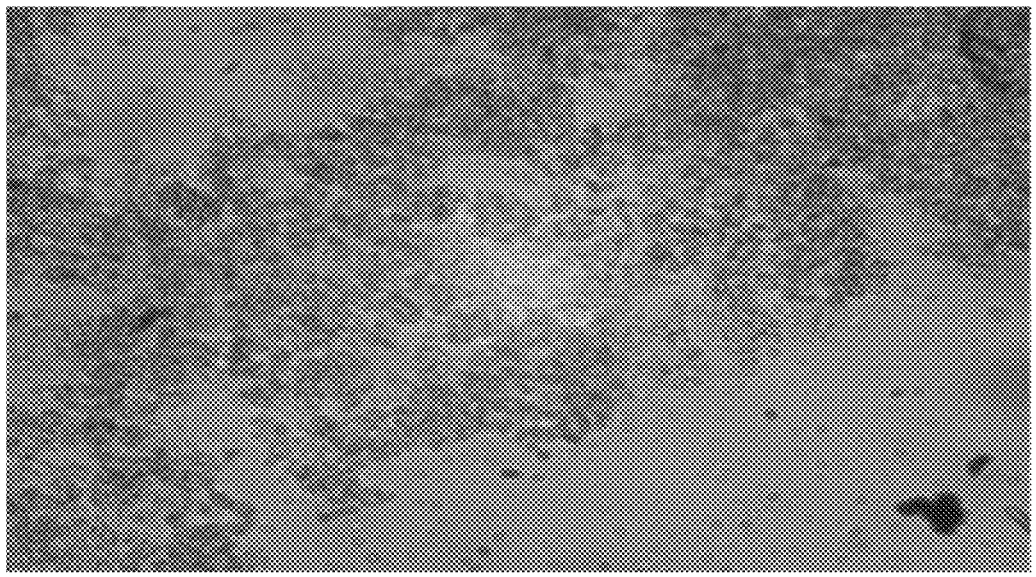
FIG. 1 is an image of a sample having asphaltenes and paraffinic components therein where a wavelength within the visible range of light was transmitted in conjunction with the optical microscopy technique.

It has been discovered that an optical microscope may be combined with an imaging device to produce images of polynuclear aromatic hydrocarbons in the near infrared spectrum. The microscopy technique applied by the optical microscope may be, but is not limited to laser confocal microscopy, fluorescence microscopy, optical microscopy, and combinations thereof. In one non-limiting embodiment, the methods may optionally use fluorescence spectroscopy by applying a grating filter and coupling this to the imaging device; however, the methods may be performed in the absence of fluorescence spectroscopy.

Confocal microscopy is an optical imaging technique used to increase optical resolution and contrast of a micrograph by using point illumination and a spatial pinhole to eliminate out-of-focus light in specimens that are thicker than the focal plane. It enables the reconstruction of three-dimensional structures from the obtained images.

Fluorescence microscopy illuminates a sample with a particular wavelength of light, which may cause the sample to fluoresce. The light emitted by fluorescence is a longer wavelength than the wavelength of light for illumination, and the emitted light may then be visualized through a microscope. Two filters are normally used for fluorescence microscopy, such as an illumination filter (also known as an excitation filter) and an emission filter (also known as an excitation filter). The illumination filter ensures the illumination to be near monochromatic and at the correct wavelength. The emission filter may ensure none of the excitation light source reaches the detector or microscope.

Optical microscopy involves passing visible light transmitted through or reflected from the sample through a single or multiple lense to allow a magnified view of the sample. It may involve or include the use of polarized or non-polarized light. The single lens with its attachments, or the system of lenses and imaging equipment, along with the appropriate lighting equipment, sample stage and support, makes up the basic light or optical microscope.

In one non-limiting embodiment, the optical microscope may include a narrowband filter to enhance contrast of emissions and/or decrease the background noise. A wavelength ranging from about 700 nm independently to about 2500 nm may be passed through the optical microscope to view images of polynuclear aromatic hydrocarbons within an oilfield fluid, and the imaging device may capture at least one image as seen by the microscope. The microscope may be any optical microscope, such as but not limited to, a metallurgical microscope, biological microscope, inverted microscope, laser confocal microscope, fluorescence microscope, and combinations thereof. The optical microscope may have an optional polarizer, such as but not limited to a single polarizer, to allow for cross polarization in the visible range of light with other spectral regions as useable with the methods.

A drop of the fluid may be placed on a normal microscope glass slide and covered with a cover slide, which spreads the drop across the glass slide into a thin film. Once placed under the microscope, the polynuclear aromatic hydrocarbons may be observed and/or imaged. The fluid does not need to be conditioned or otherwise pretreated, although there are techniques known to those skilled in the art to enhance the visualization of any polynuclear aromatic hydrocarbons within the fluid. The polynuclear aromatic hydrocarbons may even be visualized within very dark fluids as these types of fluids transmit well in the infrared region.

The imaging device may be a computer having imaging capabilities (including, but not necessarily limited to, a desktop computer, a laptop computer, a tablet computer, etc.), a phone having imaging capabilities, any CCD or CMOS based camera, a film-based camera, a light-field camera, or almost any sensor device having a sensitivity to the near infrared region may be used. The imaging device may be coupled to the microscope by mechanical adaptors and/or focusing lenses. In one non-limiting embodiment, the imaging device may be part of the microscope instead of having an imaging device affixed thereto.

A color camera may be used without an infrared filter because of the red, green, and blue filters available. The microscope and/or the imaging device may be configured to filter the light, so that the image produced is one visualized at a wavelength ranging from about 700 independently to about 2500 nm, or alternatively from about 700 nm independently to about 1310 nm, or from about 800 nm independently to about 950 nm in another non-limiting embodiment. "Independently" as defined herein means that any lower threshold may be used together with any upper threshold to give a suitable alternative range.

In another non-limiting embodiment, select filters may be added to the microscope and/or the imaging device for filter wavelengths at 700 nm, 750 nm, 800 nm, 900 nm, 1310 nm, and/or 1550 nm. These select filters may allow the microscope and/or the imaging device to distinguish the polynuclear aromatic degree of condensation of each PAH. The degree of condensation refers to the number of condensed aromatic rings that share two carbons. This is a measurement of delocalization of the molecule and of the degree of carbon to hydrogen ratio, which helps to determine the type of polynuclear aromatic hydrocarbon, such as coke in one non-limiting embodiment.

The imaging device and the microscope may allow for the visualization of polynuclear aromatic hydrocarbons such as, but not limited to, asphaltenes, coke, coke precursors, naphthalene, perylene, coronene, chrysene, anthracene, and combinations thereof. In another non-limiting embodiment, the imaging system may allow for visualization of two or more condensed aromatic rings. The polynuclear aromatic hydrocarbons may be the product of a reaction, such as but not limited to a Diels Alder reaction, free radical polymerization, asphaltene thermal cracking, de-hydrogenation, hydrocracking, and combinations thereof where at least one reactant for such a reaction may be derived from the oilfield fluid. Each polynuclear aromatic hydrocarbon may have a molecular weight ranging from about 700 g/mol independently to about 8000 g/mol, or alternatively from about 1000 g/mol independently to about 2500 g/mol, or from about 1200 g/mol independently to about 1500 g/mol in another non-limiting embodiment.

The number of rings within each polynuclear aromatic hydrocarbon may range from about 2 rings independently to about 20 rings, or alternatively from about 4 rings independently to about 6 rings. Each polynuclear aromatic hydrocarbon may have a carbon to hydrogen ratio ranging from about 0.70 carbon independently to about 2 carbon and 0.5 hydrogen independently to about 1.4 hydrogen.

A sample may be collected from an oilfield fluid that may include the polynuclear aromatic hydrocarbons. The oilfield fluid may be or include, but is not limited to, a drilling fluid, a completion fluid, a production fluid, a servicing fluid, a crude oil, a refinery fluid, and combinations thereof. 'Refinery fluid' is defined herein to be any fluid that is treated or further processed in a refinery. The amount of the polynuclear aromatic hydrocarbons within the oilfield fluid may range from about 0.1 wt % independently to about 50 wt %, or alternatively from 0.5 wt % independently to about 15 wt %, or from about 2 wt % independently to about 10 wt % in another non-limiting embodiment.

The invention will be further described with respect to the following Figures, which are not meant to limit the invention, but rather to further illustrate the various embodiments.

With respect to FIG. 1, a sample was precipitated from crude oil by heptane dosing and then a visible range of light was used in conjunction with the optical microscopy technique. The microscope was a Euromex optical microscope model ME.2665 with a Thorlabs monochrome USB CMOS camera model DCC1545M mounted thereon as the imaging device. The wavelength of light used was about 800 nm. The asphaltenes and paraffinic components were visible within the sample. However, it was hard to bring the details of the asphaltenes and paraffinic components into focus within the image.

Figure 2:
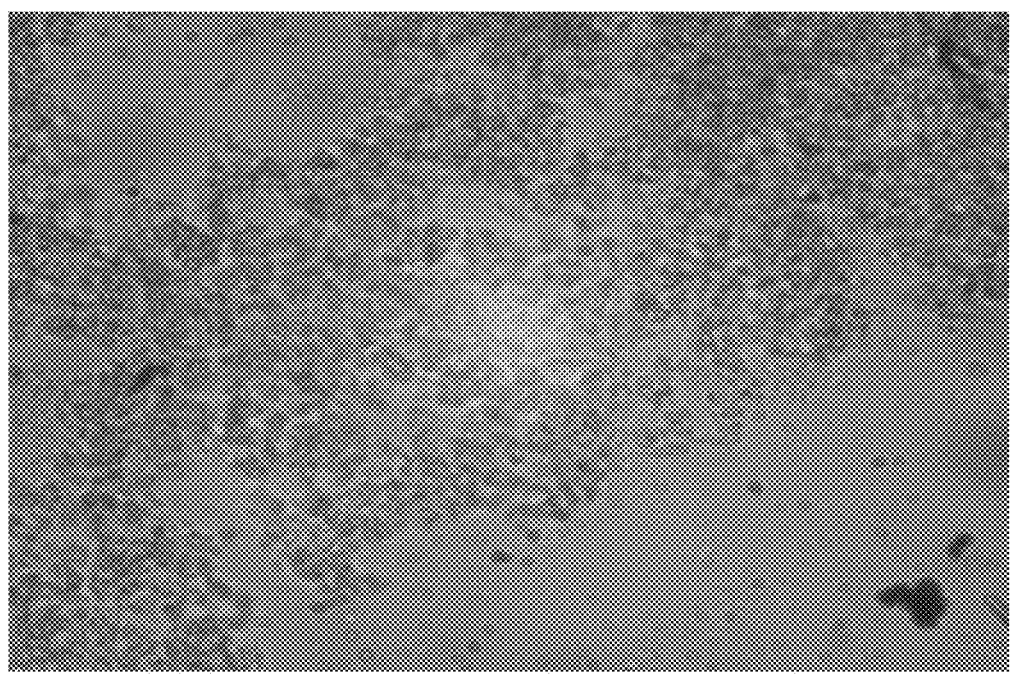
FIG. 2 is an image of the same sample as that of FIG. 1 where a wavelength within the near infrared (NIR) range of light was transmitted in conjunction with the optical microscopy technique.

FIG. 2 is an image of the same sample as that of FIG. 1, but near infrared (NIR) imaging was used, i.e. a wavelength of light of about 800 nm was transmitted in conjunction with the optical microscopy technique. The microscope was a Euromex optical microscope model ME.2665 with a Thorlabs monochrome USB CMOS camera model DCC1545M mounted thereon as the imaging device. Here, the paraffinic components become almost transparent compared to FIG. 1, but the PAHs having from about four to about five condensed rings are more contrasted.

Figure 3:
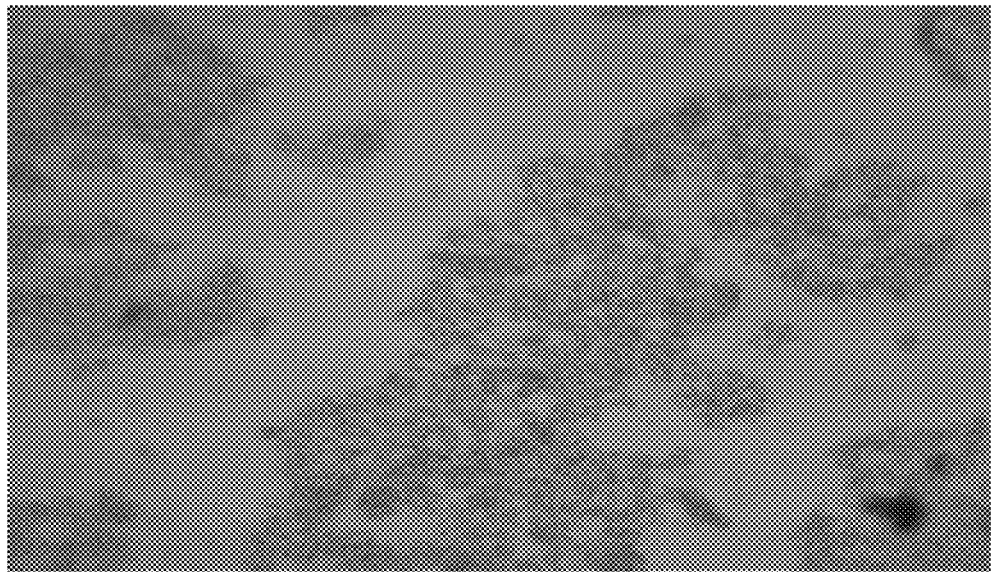
FIG. 3 is a second image of a sample having asphaltenes and paraffinic components therein where a wavelength within the visible range of light was transmitted in conjunction with the optical microscopy technique.

FIG. 3 illustrates a second sample having asphaltenes and paraffinic components where the sample was precipitated from crude oil by heptane dosing. The microscope was a Euromex optical microscope model ME.2665 with a Thorlabs monochrome USB CMOS camera model DCC1545M mounted thereon as the imaging device. A visible range of light was used in conjunction with the optical microscopy technique, and a 800 nm wavelength was transmitted through the optical microscope. Similar to FIG. 1, it was difficult to focus the details of the asphaltenes and paraffinic components within the image.

Figure 4:
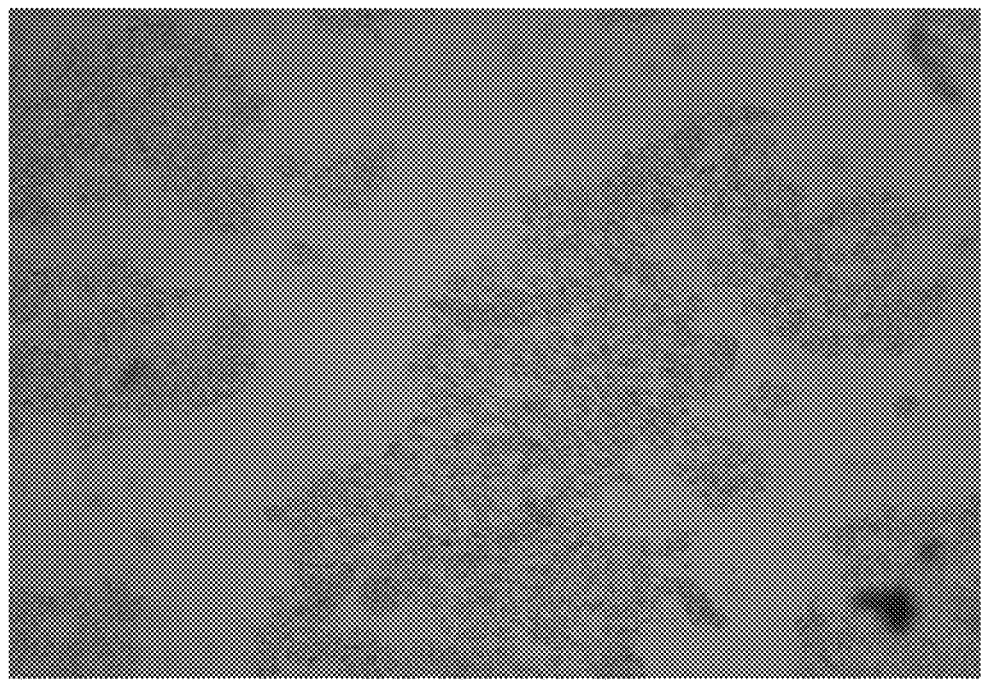
FIG. 4 is an image of the same sample as that of FIG. 3 where a wavelength within the near infrared (NIR) range of light was transmitted in conjunction with the optical microscopy technique.

FIG. 4 is an image of the same sample as that of FIG. 3, but NIR imaging was used, i.e. a wavelength of light of about 800 nm was transmitted in conjunction with the optical microscopy technique. The microscope was a Euromex optical microscope model ME.2665 with a Thorlabs monochrome USB CMOS camera model DCC1545M mounted thereon as the imaging device. Here, the paraffinic components have a more focused structure where the PHA zones are contrasted with a black structure when compared to FIG. 3.

In the foregoing specification, the invention has been described with reference to specific embodiments thereof, and has been described as effective in providing methods for producing and capturing an image of polynuclear aromatic hydrocarbons by using the near infrared spectrum of light.

However, it will be evident that various modifications and changes can be made thereto without departing from the broader spirit or scope of the invention as set forth in the appended claims. Accordingly, the specification is to be regarded in an illustrative rather than a restrictive sense. For example, specific microscopes, imaging devices, polynuclear aromatic hydrocarbons, oilfield fluids, wavelengths, and microscopy techniques, falling within the claimed parameters, but not specifically identified or tried in a particular composition or method, are expected to be within the scope of this invention.

The present invention may suitably comprise, consist or consist essentially of the elements disclosed and may be practiced in the absence of an element not disclosed. For instance, the method may consist of or consist essentially of a method for producing an image of polynuclear aromatic hydrocarbons with an optical microscope by passing a wavelength ranging from about 700 nm to about 2500 nm therethrough, and capturing the image produced by the microscope with an imaging device.

The words "comprising" and "comprises" as used throughout the claims, are to be interpreted to mean "including but not limited to" and "includes but not limited to", respectively.

What is claimed is:

1. A method comprising: producing an image of polynuclear aromatic hydrocarbons with an optical microscope by passing a wavelength ranging from about 700 nm to about 2500 nm therethrough; and capturing the image produced by the microscope with an imaging device; and distinguishing a number of condensed aromatic rings that share two carbons for each polynuclear aromatic hydrocarbon within a compound selected from the group consisting of asphaltenes, coke, coke precursors, naphthalene, perylene, coronene, chrysene, anthracene, and combinations thereof.

2. The method of claim 1, wherein the polynuclear aromatic hydrocarbons are within a compound selected from the group consisting of coke, coke precursors, naphthalene, perylene, coronene, chrysene, anthracene, and combinations thereof.

3. The method of claim 1, wherein a sample comprising the polynuclear aromatic hydrocarbons has been collected from an oilfield fluid selected from the group consisting of a drilling fluid, completion fluid, production fluid, servicing fluid, crude oil, a refinery fluid, and combinations thereof.

4. The method of claim 3, wherein the amount of the polynuclear aromatic hydrocarbons within the oilfield fluid ranges from about 0.1 wt % to about 50 wt %.

5. The method of claim 1, wherein each polynuclear aromatic hydrocarbon has a molecular weight ranging from about 700 g/mol to about 8000 g/mol.

6. The method of claim 1, wherein the number of rings within each polynuclear aromatic hydrocarbon ranges from about 2 rings to about 20 rings.

7. The method of claim 1, wherein the optical microscope applies a microscopy technique selected from the group consisting of laser confocal microscopy, fluorescence microscopy, optical microscopy, and combinations thereof.

8. The method of claim 1, wherein the imaging device is configured to filter a wavelength ranging from about 700 nm to about 2500 nm.

9. The method of claim 1, wherein each polynuclear aromatic hydrocarbon has a carbon to hydrogen ratio ranging from about 0.7 carbon to about 2 carbon and 0.5 hydrogen to about 1.4 hydrogen.

10. A method comprising:
producing an image of polynuclear aromatic hydrocarbons with an optical microscope by passing a wavelength ranging from about 700 nm to about 2500 nm therethrough; wherein the polynuclear aromatic hydrocarbons are within a compound selected from the group consisting of coke, coke precursors, naphthalene, perylene, coronene, chrysene, anthracene, and combinations thereof;
capturing the image produced by the microscope with an imaging device, wherein the imaging device is configured to filter a wavelength of about 700 nm to about 2500 nm therethrough;
distinguishing a number of condensed aromatic rings that share two carbons for each polynuclear aromatic hydrocarbon within a compound selected from the group consisting of coke, coke precursors, naphthalene, perylene, coronene, chrysene, anthracene, and combinations thereof; and
wherein a sample comprising the polynuclear aromatic hydrocarbons has been collected from an oilfield fluid selected from the group consisting of a drilling fluid, completion fluid, production fluid, servicing fluid, crude oil, refinery fluid, and combinations thereof.

11. The method of claim 10, wherein the amount of the polynuclear aromatic hydrocarbons within the oilfield fluid ranges from about 0.1 wt % to about 50 wt %.

12. The method of claim 10, wherein each polynuclear aromatic hydrocarbon has a molecular weight ranging from about 700 g/mol to about 8000 g/mol.

13. The method of claim 10, wherein the number of rings within each polynuclear aromatic hydrocarbon ranges from about 2 rings to about 20 rings.

14. The method of claim 10, wherein the optical microscope applies a microscopy technique selected from the group consisting of laser confocal microscopy, fluorescence microscopy, optical microscopy, and combinations thereof.

15. The method of claim 10, wherein the carbon to hydrogen ratio of each polynuclear aromatic hydrocarbon ranges from about 0.7 carbon to about 2 carbon and 0.5 hydrogen to about 1.4 hydrogen.

16. An apparatus comprising an optical microscope, an imaging device, and combinations thereof; wherein the optical microscope is selected from the group consisting of a metallurgical microscope, biological microscope, inverted microscope, laser confocal microscope, fluorescence microscope, and combinations thereof; and wherein the imaging device comprises a CCD detector having a high sensitivity for a wavelength ranging from about 650 nm to about 2500 nm;
where the optical microscope is configured to apply a microscopy technique selected from the group consisting of laser confocal microscopy, fluorescence microscopy, optical microscopy, and combinations thereof to distinguish a number of condensed aromatic rings that share two carbons for each polynuclear aromatic hydrocarbon within a compound selected from the group consisting of asphaltenes, coke, coke precursors, naphthalene, perylene, coronene, chrysene, anthracene, and combinations thereof.

17. The apparatus of claim 16, wherein the optical microscope further comprises a narrowband filter.

* * * * *